United States Patent [19]

Kammerer et al.

[11] Patent Number: 5,282,809
[45] Date of Patent: Feb. 1, 1994

[54] ENDOSCOPIC SUTURING DEVICE

[75] Inventors: Gene W. Kammerer, East Brunswick; Royce Frederick, South Bound Brook, both of N.J.

[73] Assignee: Ethicon, Inc., Somerville, N.J.

[21] Appl. No.: 976,788

[22] Filed: Nov. 16, 1992

[51] Int. Cl.⁵ ............................................. A61B 17/04
[52] U.S. Cl. ................................................ 606/148
[58] Field of Search .................... 606/148, 139, 113

[56] References Cited

U.S. PATENT DOCUMENTS

| 529,936 | 11/1894 | McNalley | 606/113 |
| 2,012,776 | 8/1935 | Roeder . | |
| 3,926,194 | 12/1975 | Greenberg et al. | 606/227 |
| 5,129,912 | 7/1992 | Noda et al. | 606/139 |
| 5,144,961 | 9/1992 | Chen et al. | 128/898 |

FOREIGN PATENT DOCUMENTS 0420605 4/1991 European Pat. Off. .
0477020 3/1992 European Pat. Off. .

OTHER PUBLICATIONS

Endoknot, Suture Made with Chromic Gut, Ethicon, Inc., 1991.

Primary Examiner—Stephen C. Pellegrino
Assistant Examiner—Tamara L. Graysay
Attorney, Agent, or Firm—Paul A. Coletti

[57] ABSTRACT

A suturing device for placing a continuous suture line between anchor knots is disclosed. The device has a cannula and first and second sutures. Each suture has a slide end, a distal loop, and a slip knot securing the distal loop to the slide end. The sutures are threaded through the cannula. One of the sutures has a stay end extending from the slip knot, and a needle attached to this stay end. The device is particularly adapted to place a continuous suture line during endoscopic surgical procedures.

13 Claims, 8 Drawing Sheets

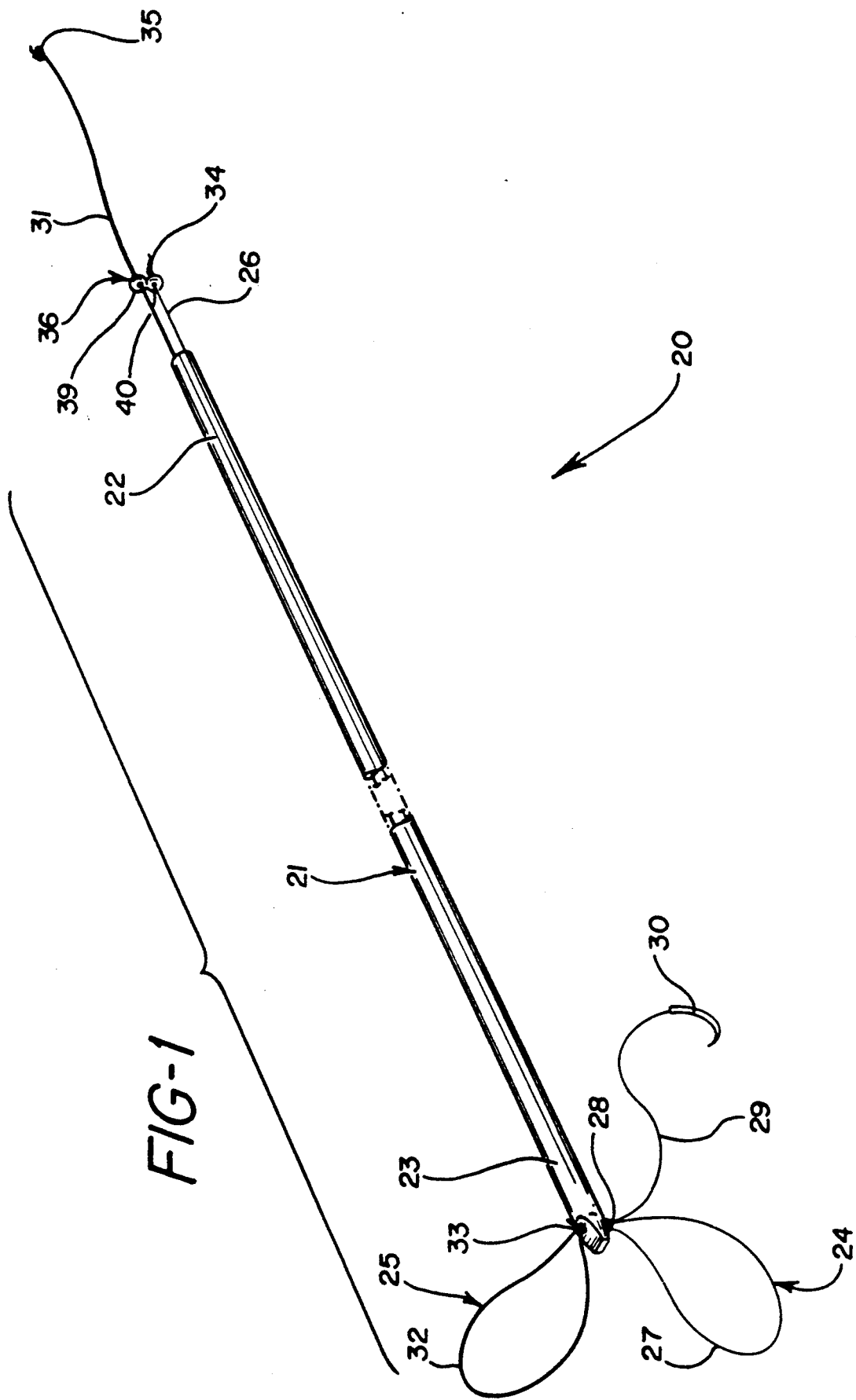

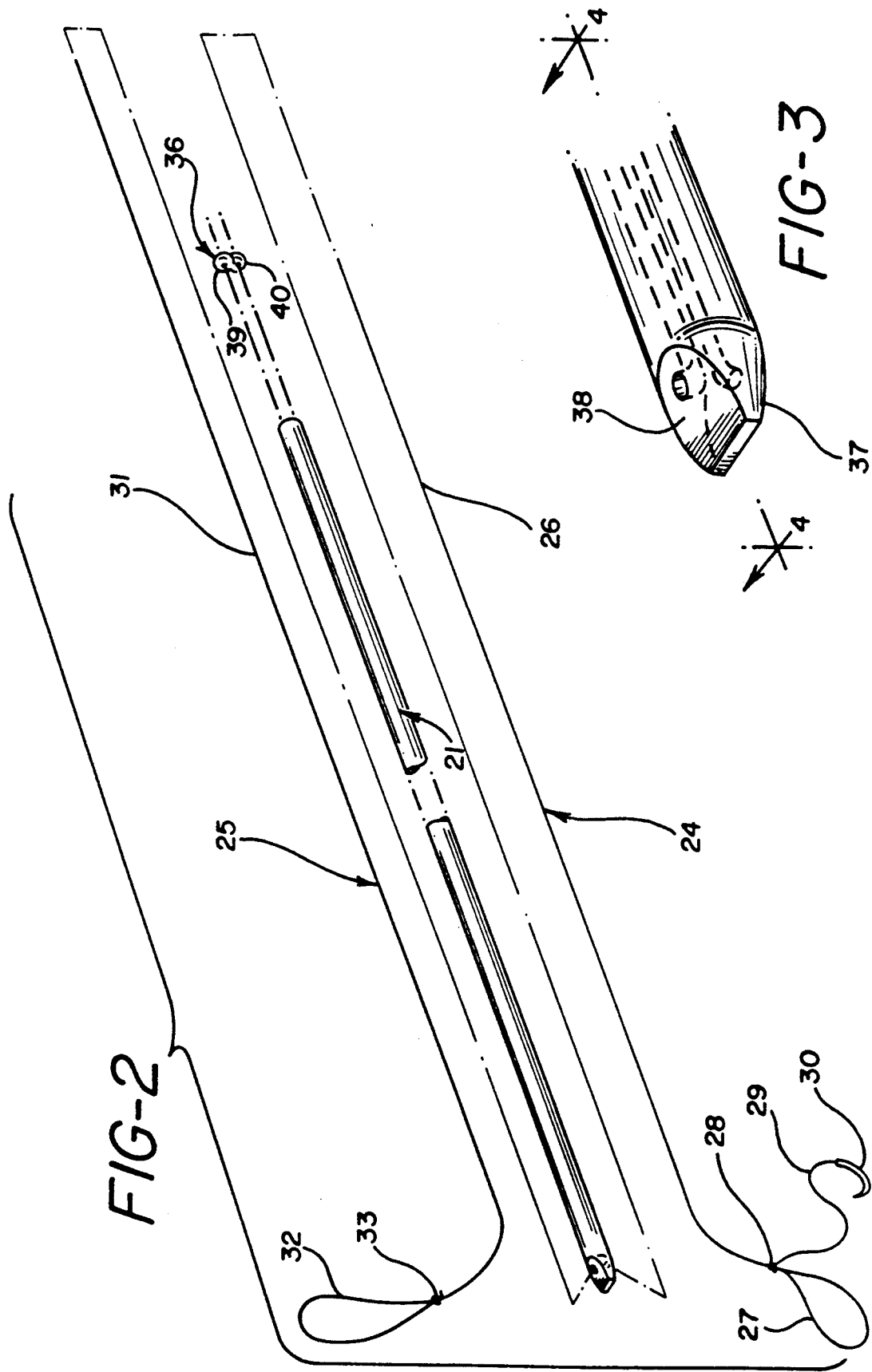

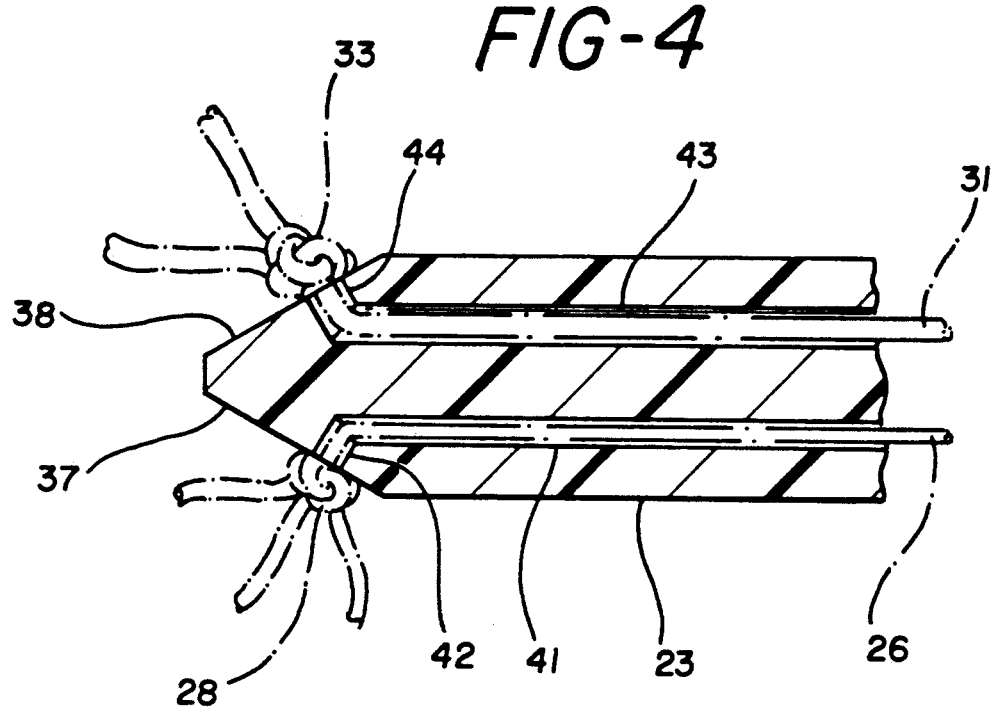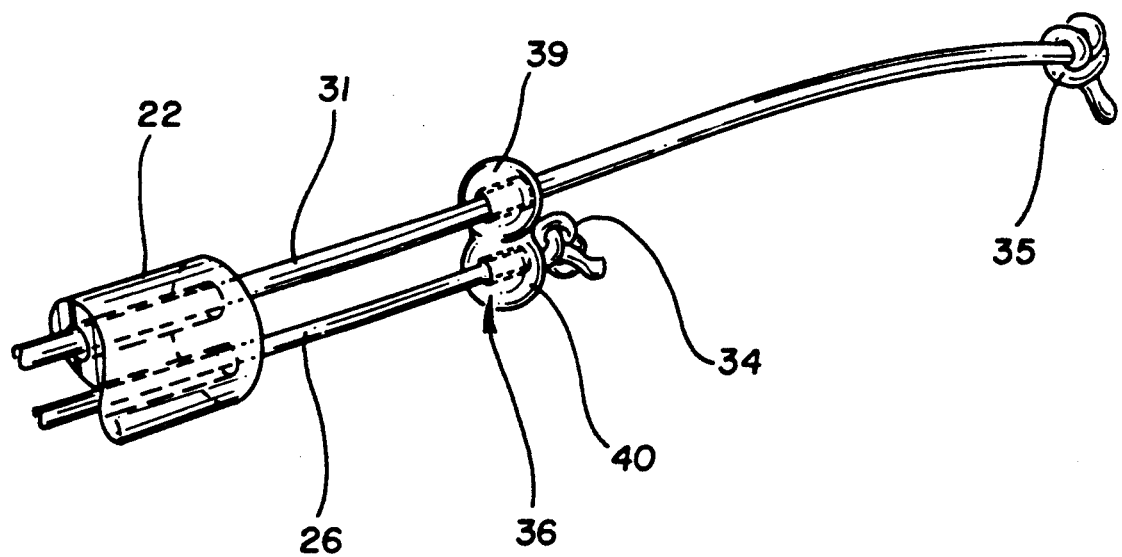

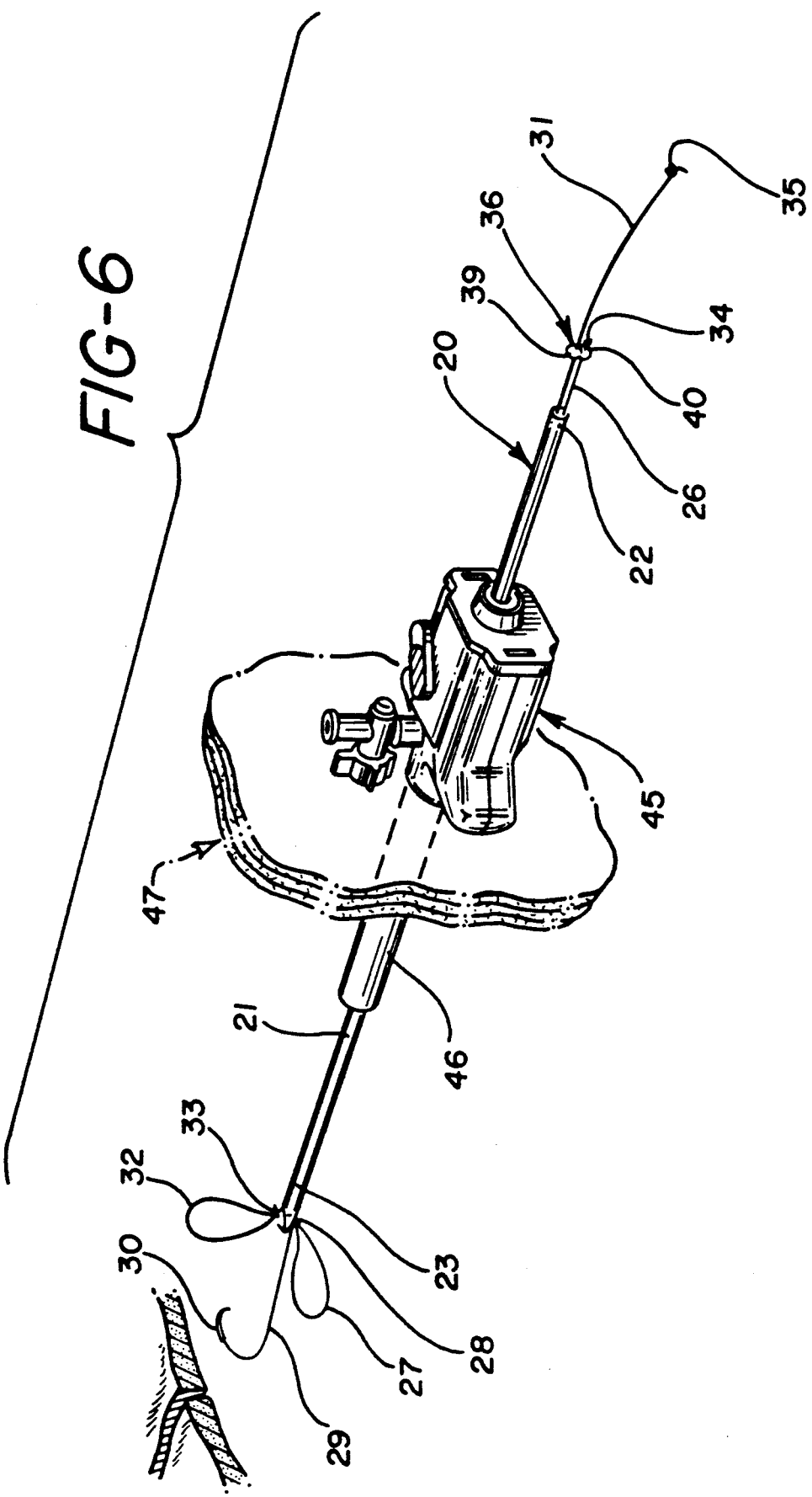

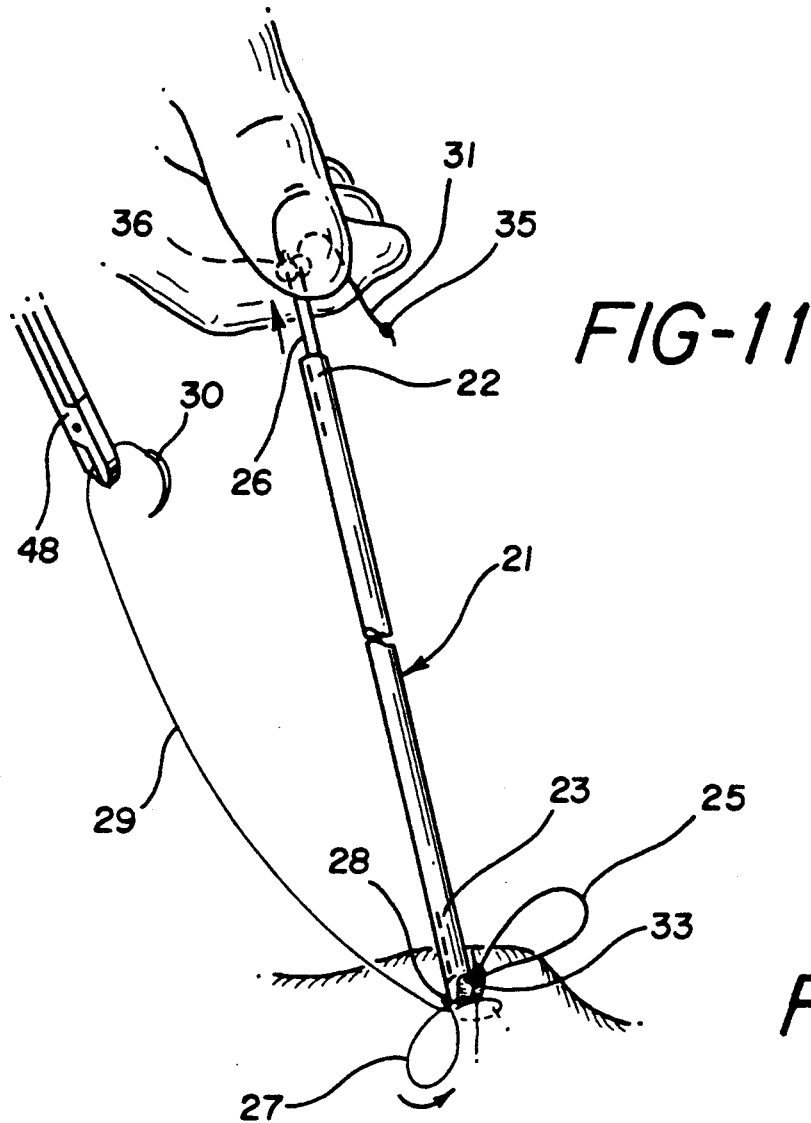
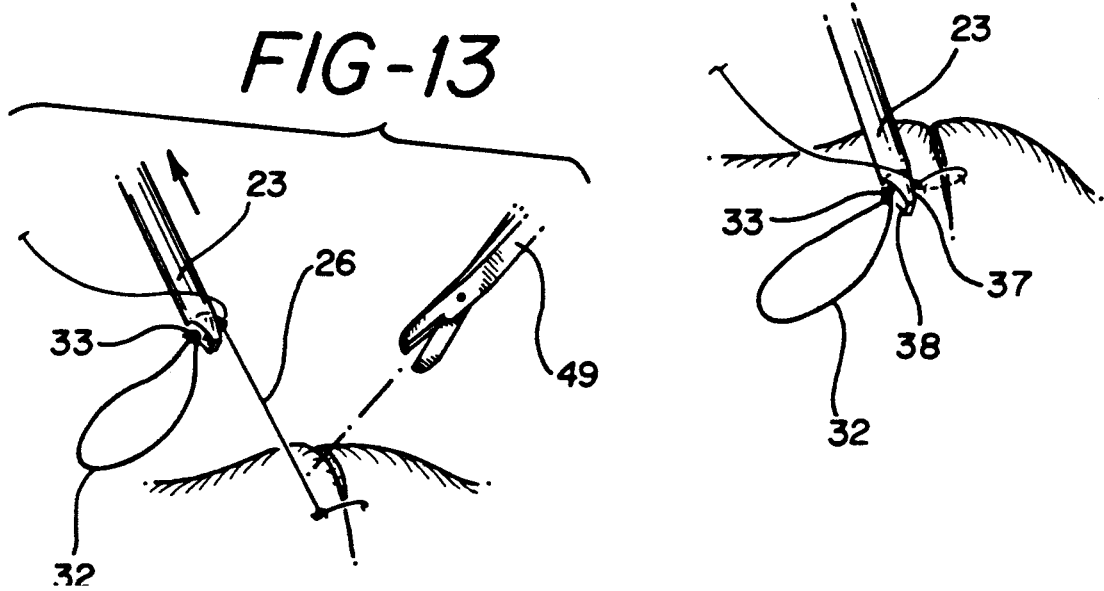

ENDOSCOPIC SUTURING DEVICE

BACKGROUND OF THE INVENTION

This invention relates to a suturing device for joining severed bodily tissue, particularly one adapted for endoscopic surgical procedures.

One of the truly great advances in recent years to reduce the invasiveness of surgical procedures is endoscopic surgery. Endoscopic surgery involves the use of an endoscope, which is an instrument permitting the visual inspection and magnification of any cavity of the body. The endoscope is inserted through a tube, conventionally referred to as a cannula, after puncture of a hole into the soft tissue protecting the body cavity. The hole is made with a trocar, which is a sharp-pointed instrument. The trocar includes an obturator, or cutting implement, which is slidably and removably disposed within a trocar cannula. The obturator will puncture a hole in the tissue equal in size to the inner diameter of the trocar cannula. After puncture, the obturator can be slidably withdrawn from the trocar cannula. The surgeon can then perform diagnostic and therapeutic procedures at the surgical site with the aid of specialized instrumentation designed to fit through the trocar cannula and additional trocar cannulas providing openings into the desired body cavity as may be required.

In many surgical procedures, suturing is required to close wounds. The severed tissue often requires several stitches to join the severed tissue along the length of the laceration. The stitches require an anchor knot at the beginning and end of the line of stitches for proper support during the healing period. As the reader will readily appreciate, it is difficult to tie knots endoscopically. Accordingly, numerous devices have been proposed to accomplish this task or similar tasks. See, for example, the 1991 package insert for the product sold by Ethicon, Inc., which insert is entitled "ENDOKNOT Suture Made With Chromic Gut"; European Patent Application 477,020, published Mar. 25, 1992; U.S. Pat. No. 5,129,912; U.S. Pat. No. 5,144,961; and U.S. Pat. No. 2,012,776.

All of the devices described in these references use a cannula for insertion through a trocar, to which is attached a suture configuration maneuverable for the placement of a knot. For example, the suture may have a pre-loop formation which only requires tightening to secure the knot. The most recent device is described in copending application Ser. No. 947,662, filed Sep. 18, 1992, which has a cannula with a beveled tip for easily maneuvering and rotating the pre-loop suture formation.

Unfortunately, the devices described in the art have a major drawback. While these devices make it easier to tie an anchor knot, more features are needed for suturing. This is because in addition to the placement of anchor knots, several stitches need to be placed to make a continuous suture line for joining the severed tissue along the length of the laceration. Although the described devices eliminate the need for manually tying knots extracorporeally (outside the body), and are designed to easily position the suture formation, nothing is provided for placing a continuous line of stitches when the device is positioned at the location of the severed bodily tissue.

In view of the significant deficiency of the art, an endoscopic suturing device which is designed not only to avoid manually tying knots extracorporeally but also to place several secure stitches in a continuous suture line, would be highly desired within the medical community.

SUMMARY OF THE INVENTION

The invention is a suturing device. It comprises a cannula, and first and second sutures.

The first suture has a first slide end, a first distal loop, and a first slip knot which secures the first distal loop to the first slide end. A stay end of the first suture extends from the first slip knot, and a needle is attached to the stay end. The first slide end is threaded through the cannula.

The second suture has a second slide end, and a second slip knot securing the second distal loop to the second slide end. The second slide end is threaded through the cannula.

This device is capable of not only eliminating the need for tying an anchor knot extracorporeally, but also placing several stitches securely in a continuous suture line. In this manner, severed tissue can be properly joined along the entire length of the laceration. The device enables the user to place an anchor knot at the beginning of the suture line, make several stitches to join the severed tissue, and then anchor those stitches with an additional anchor knot at the end of the continuous suture line. All of these procedures can be performed endoscopically without removing the device from the internal surgical site.

In a preferred embodiment of the invention, the first and second distal loops of the sutures are displayed adjacent to first and second opposed beveled surfaces, respectively, at the distal end of the cannula. The positioning of the loops in this manner improves the ease with which the loops can be maneuvered and positioned for the convenient and quick placement of the anchor knots.

The device of this invention can be used in any surgical procedure, including open surgery, when it is necessary to join severed tissue. The device is especially adapted for use during surgery in remote locations with reduced surgeon access, for example during endoscopic surgical procedures.

BRIEF DESCRIPTION OF THE DRAWINGS

FIG. 1 is a perspective view of the preferred suturing device of this invention.

FIG. 2 is an exploded perspective view of the preferred suturing device.

FIG. 3 is an enlarged fragmentary perspective view of the distal end of the cannula prior to threading the first and second sutures through the cannula.

FIG. 4 is a cross-sectional view of the distal end of the cannula as taken along line 4—4 of FIG. 3.

FIG. 5 is an enlarged fragmentary view of the proximal end of the cannula.

FIG. 6 is a perspective view of the preferred suturing device of this invention shown inserted into a trocar for access to a desired surgical site.

FIGS. 7-17 are perspective views showing the sequence of steps for placing a continuous row of stitches to close a wound.

DETAILED DESCRIPTION OF THE PREFERRED EMBODIMENT

Figure 7:
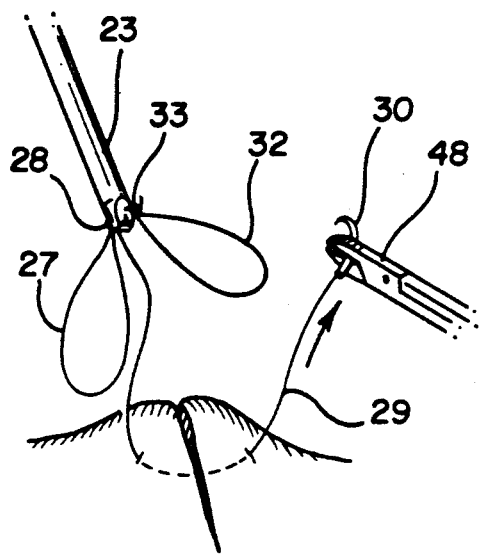

As used in this specification, the word "distal" is used to describe that portion of the device which extends away from the user during use, and the word "proximal" is used to describe that portion of the device that extends toward the user during use. Similarly, "distally" refers to movement extending away from the user during use of the device, and "proximally" refers to movement extending toward the user.

Referring now to the drawings, and particularly FIG. 1, there is shown the preferred suturing device 20. The suturing device has a cannula 21 with proximal and distal ends 22 and 23, respectively. It also includes first and second sutures 24 and 25, respectively.

The first suture has a first slide end 26 protruding from the proximal end of the cannula, and a first distal loop 27 protruding from the distal end of the cannula. This first distal loop is secured to the first slide end with first slip knot 28. Extending from the first slip knot is stay end 29 of the suture. A surgical needle 30 is attached to this stay end.

The second suture 25 similarly has a second slide end 31 protruding from the proximal end of the cannula, and a second distal loop 32 protruding from the distal end of the cannula. This loop is secured to the second slide end with a second slip knot 33.

The first and second slide ends of the sutures terminate with first and second proximal knots 34 and 35, respectively. Grasping means 36 are slidably attached to the first and second slide ends between the proximal end of the cannula and the first proximal knot. A more detailed explanation of the grasping means is provided in conjunction with the description of FIG. 4 below.

The incorporation of the first and second sutures 24 and 25, respectively, into cannula 21 to form the preferred device is illustrated at FIG. 2. The slide ends of the sutures are threaded completely through the cannula until the slip knots make contact with the distal end of the cannula. The slide ends of the sutures are long enough so that they protrude from the proximal end of the cannula when the slip knots make contact with the cannula.

The distal end of the cannula for the preferred suturing device has the configuration shown in FIG. 3. The distal end terminates with a first beveled surface 37, and a second opposed beveled surface 38. The channels through which the first and second slide ends of the sutures are threaded extend from the first and second beveled surfaces to the proximal end of the cannula, as will be explained in more detail with respect to FIG. 5.

Figure 8:
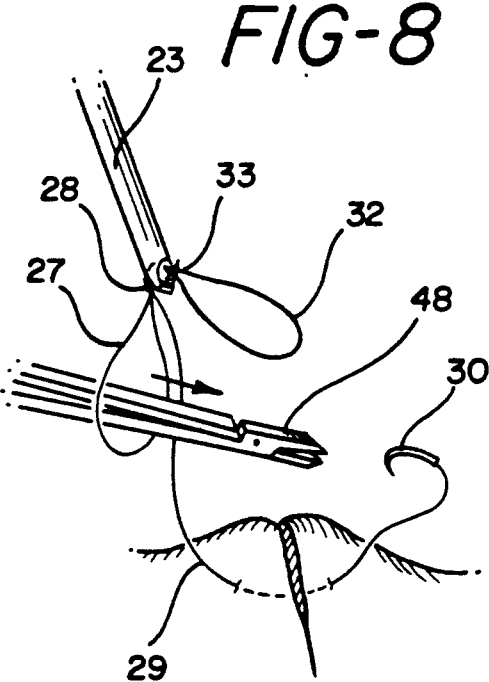
Figure 9:
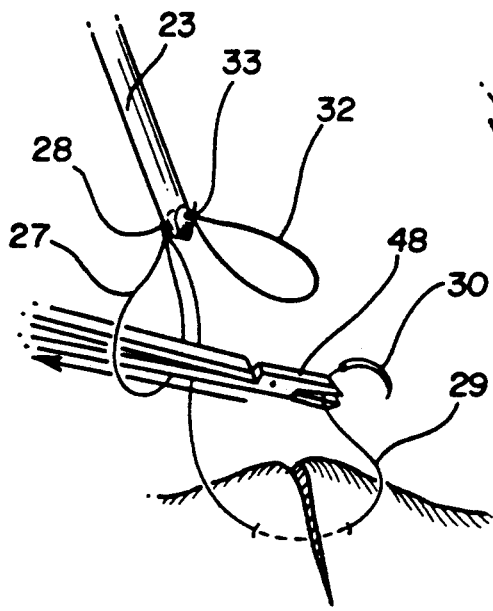
Figure 10:
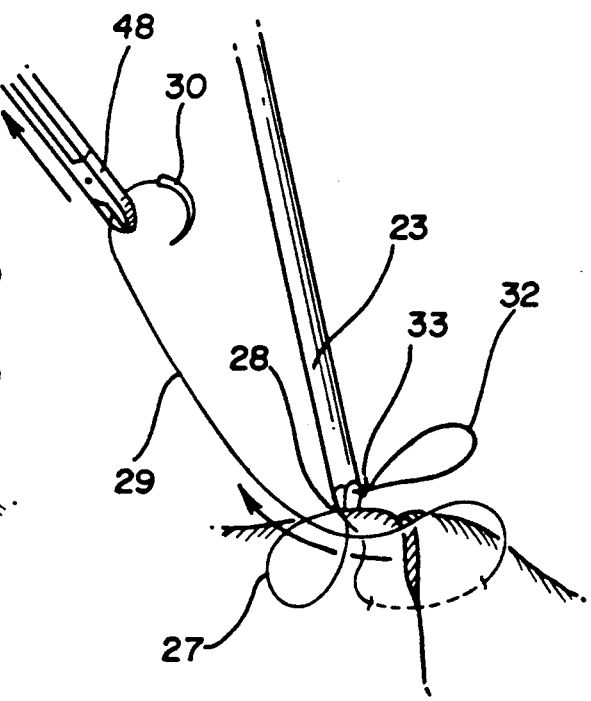
Figure 14:
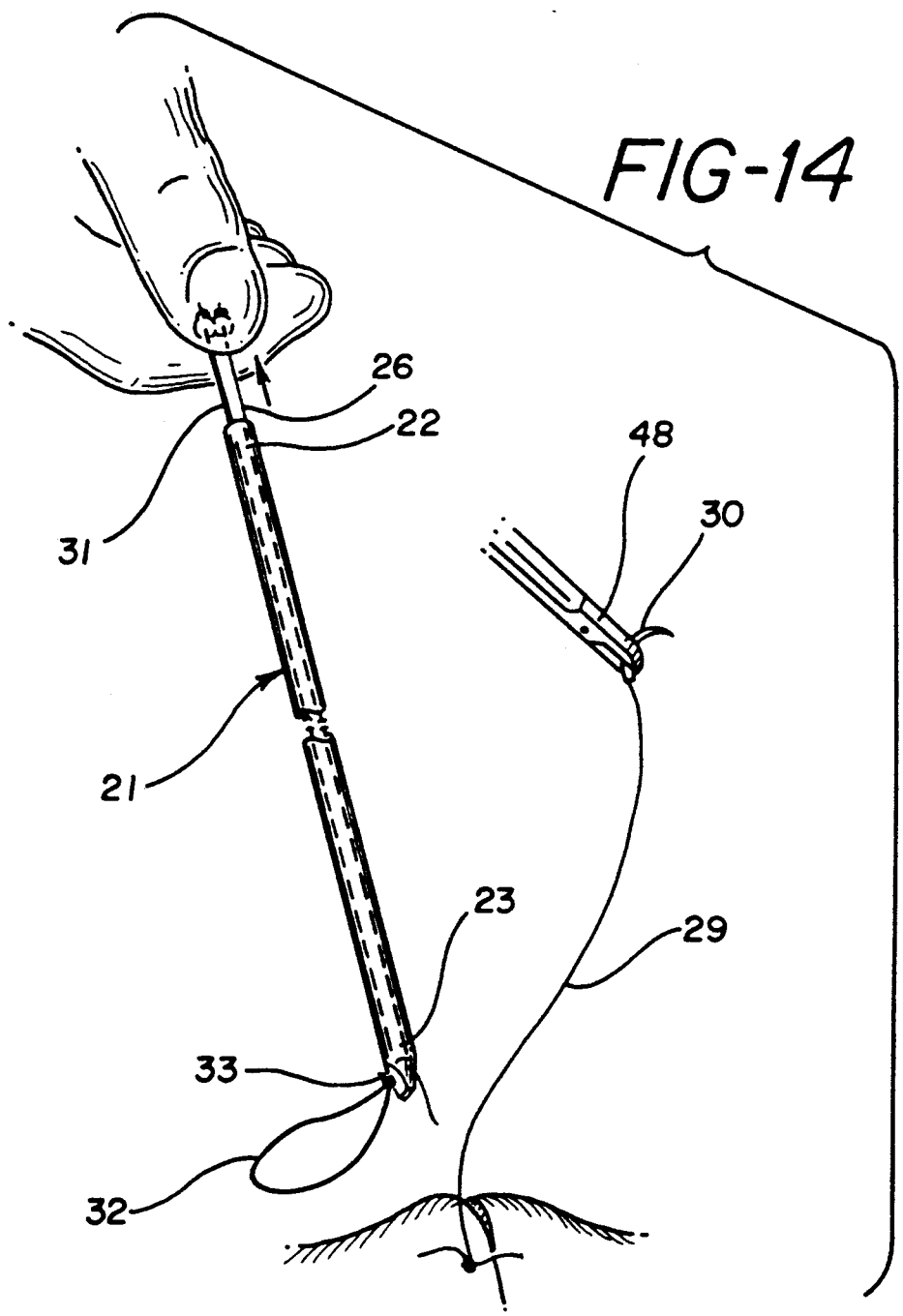
Figure 15:
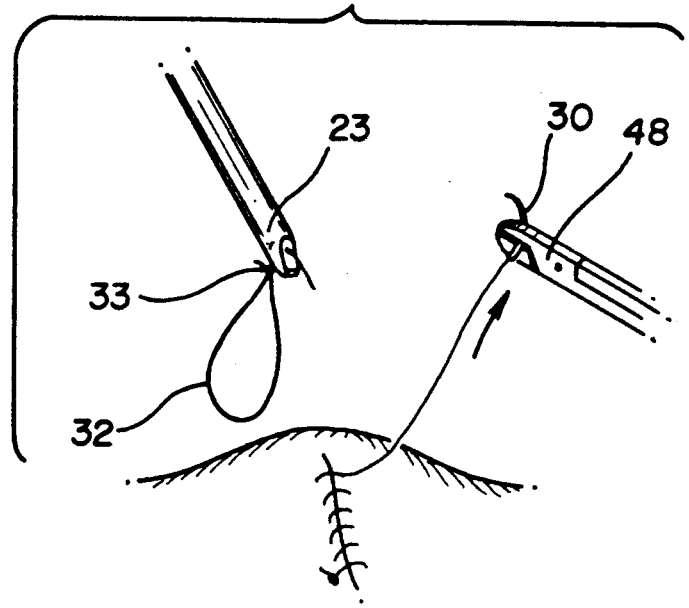
Figure 16:
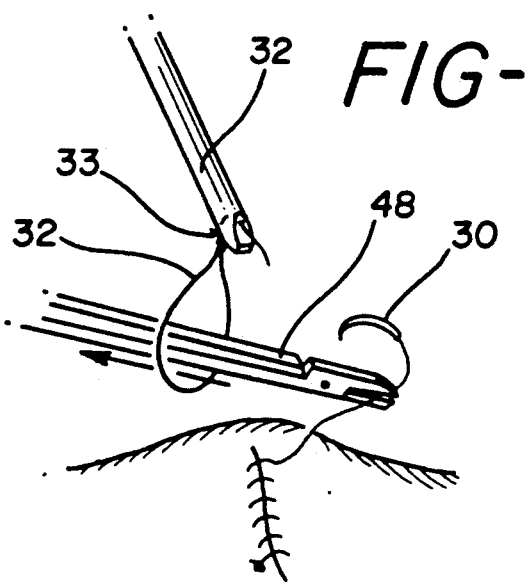
Figure 17:

The grasping means 36 attached to that portion of the slide ends of the sutures which protrude from the proximal end of the cannula is a molded pair of first and second nylon beads 39 and 40, as shown in FIG. 5. The beads are sized to help the surgeon readily grasp the first and second slide ends of the sutures, and to pull the slide ends proximally to close the first and second distal loops during surgery. Each bead has an aperture running through it so that the bead can freely slide between the proximal end of the cannula and the first proximal knot 34. When the surgeon pulls the molded pair of beads proximally, the beads initially pull against the first proximal knot, and consequently the first slide end 26 is pulled proximally until the first distal loop is fully closed. The second suture is sized so that its slide end is sufficiently longer than the first slide end to prevent pulling contact of the beads against the second proximal knot 35 when the first distal loop is being closed. After the first distal loop is closed, the first slide end is cut away to enable the surgeon to pull the beads proximally against the second proximal knot 35 to close the second distal loop, as will be explained in more detail with respect to FIGS. 7–17. The proximal knots are sized in relation to the apertures within the beads to prevent the beads from being pulled off of the first and second slide ends of the suture. Similarly, the beads themselves are sized in relation to the channels running through the cannula to prevent the beads from sliding inside the cannula.

The first and second slide ends of the sutures are threaded through separate and independent channels extending through the cannula. Each slide end is threaded through separate first and second channels in the cannula. Referring now to FIG. 4, the first slide end of the first suture is threaded through first primary channel 41 and first secondary channel 42. The first primary channel extends axially through the cannula from the distal to the proximal end. The first secondary channel extends from the first beveled surface 37 of the cannula to the first primary channel so that what in effect is formed is a continuous opening in the cannula from the first beveled surface to the proximal end of the cannula. The angle between the first primary and secondary channels is preferably no less than about 20°, but ideally it is about 30°. Likewise, the angle between the first beveled surface and the first primary channel is preferably no less than 20°, but ideally it is about 30°. When the first slide end of the first suture is threaded through the first primary and secondary channels of the cannula, the first slip knot abuts the opening of the first secondary channel at the first beveled surface.

The threading of the second slide end of the second suture through the cannula is done in the same manner as that described for the first slide end of the first suture. Therefore, the second slide end is threaded through second primary channel 43 and secondary channel 44 to make a continuous opening in the cannula from the second beveled surface 38 to the proximal end of the cannula.

The positioning of the slip knots on the opposed beveled surfaces at the distal end of the cannula facilitates positioning of the loops during surgery for convenient placement of the anchor knots, as similarly described in copending application Ser. No. 947,662, filed Sep. 18, 1992.

The first and second sutures 24 and 25, respectively, can be composed of any surgical suture material. Suture materials can be composed of synthetic and nonsynthetic filaments, as well as absorbable and nonabsorbable fibers. Examples of suitable nonabsorbable suture materials include, but are not limited to, nylon, polypropylene, steel, and polyethyleneterephthalate (PET). The preferred sutures are synthetic bioabsorbable sutures. Examples of suitable bioabsorbable sutures are those which are derived from the polymerization of lactone monomers, e.g., glycolide, lactide, para-dioxanone and ε-caprolactone.

In a preferred embodiment of the invention, the strength of the anchor knot formed when the second distal loop is closed is increased to prevent the tightened loop from slipping back through the needle passageway in the tissue. This anchoring ability can be increased if the second suture is composed of a larger size suture strand. For example, is may be desirable to use a United States Pharmaecopia (U.S.P.) size 2/0 PDS II ® polydioxanone monofilament suture for the first suture, and then fabricate the second suture of a larger suture size, such as U.S.P. size 0 or 1 PDS II ® polydioxanone suture. An additional method of increasing the anchoring ability of the second tightened loop is to pass the surgical needle through the second loop multiple times before this loop is closed. Alternatively, a third suture with a third loop protruding from the distal end of the cannula can be incorporated into the device. If such a third loop were present, then the needle could be passed through not only the second loop but also the third loop to form an additional knot for firmly anchoring the stitches in place.

The stay end 29 of the first suture 24 extending from first slip knot 28 can be attached to the surgical needle 30 using standard needle attachment. Alternatively, it can be attached using removable or detachable needle attachment. In the case of standard needle attachment, the suture is securely attached to the needle and is not intended to be separated from the needle except by cutting or severing the strand. Removable needle attachment, by contrast, is such that the needle is separable from the strand in response to a force exerted by the surgeon, as illustrated, for example, in European Patent Application 0420605 and U.S. Pat. No. 3,926,194.

The configuration of the slip knots of the sutures can be any configuration which allows for sliding movement of their respective slide ends proximally and prevents such sliding movement distally. In this manner the slip knots serve to function as a knot which will allow for the continual reduction in the size of the distal loops of the sutures, yet prevents the enlargement of the distal loops, so that a secure and strong anchor knot can be placed on the stitched tissue.

The material of construction of the cannula 21 of the preferred device is not critical, so long as whatever material is chosen is sufficiently biocompatible with bodily tissue. A preferred material of choice for the cannula is nylon because of the ease with which it can be fabricated and its biocompatability.

To approximate tissue using the device, the surgeon would ideally first backload the cannula of the device into and through an appropriate introducer for a trocar. The introducer, with the device loaded into it, is then placed into an appropriately sized trocar. The trocar provides access into a body cavity where the desired tissue approximation is to occur. As illustrated in FIG. 6, the cannula 21 of the suturing device 20 is pushed into the field of surgery through trocar 45 and trocar cannula 46, which have penetrated bodily tissue 47.

Referring now to FIGS. 7-17 in sequence, the surgeon would use graspers 48 to hold and orient the needle, and to pass the surgical needle through the two segments of tissue to be joined. The surgeon then positions first distal loop 27 of the first suture 24 by rotating the cannula 21 of the device so that the graspers can be easily passed through the first distal loop. Once the graspers have been passed through the distal loop, the surgeon then grasps the stay end 29 of the first suture just behind the needle, and pulls the stay end and needle of the first suture through the loop. As the stay end of the suture is pulled, the cannula 21 is simultaneously advanced distally until the base of the first slip knot 28 lies against the tissue to be joined. While holding the stay end of the suture firmly, the first distal loop 27 of the first suture can now be closed to form the first anchor knot. To close the loop, the beads slidably attached to the slide ends of the sutures protruding from the proximal end of the cannula are held firmly and pulled proximally against the first proximal knot 34. As the beads are pulled proximally, the first distal loop subsequently becomes smaller and smaller until it is cinched about the first suture to form an anchor knot joining the severed tissue. Once the knot is formed, the first slide end can be severed from the knot with scissors 49. The surgeon can then place a continuous row of stitches to fully close the wound. A second anchor knot at the termination of the row of stitches is then placed using the second distal loop 32 in the same way that the first anchor knot was placed. When the suture strand is pulled through the second distal loop, and this loop is ready to be tightened to form the knot, the surgeon grasps the beads and pulls proximally against the second proximal knot until the loop is tightened. Thereafter, the second slide end is severed from the knot, and the device can be removed from the body.

Although this description has focused on the preferred embodiment of the device, it is readily apparent that numerous additional embodiments of the device can be envisioned without departing from the spirit and scope of the claimed invention.

We claim:

1. A suturing device comprising:
    a) a cannula;
    b) a first suture, said first suture having a first slide end, a first distal loop, a first slip knot securing first said distal loop to said first slide end, a stay end extending from said first slip knot, and a needle attached to said stay end, said first slide end threaded through said cannula; and
    c) a second suture, said second suture having a second slide end, a second distal loop, and a second slip knot securing said second distal loop to said second slide end, said second slide end threaded through said cannula.

2. The device of claim 1 wherein said cannula has proximal and distal ends, and said first and second distal loops protrude from said distal end.

3. The device of claim 2 wherein said distal end of said cannula has first and second opposed beveled surfaces.

4. The device of claim 3 wherein said first distal loop protrudes from said first beveled surface, and said second distal loop protrudes from said second beveled surface.

5. The device of claim 4 wherein said cannula has a first primary channel extending axially therethrough and a first secondary channel extending from said first beveled surface to said first primary channel, and said first slide end of said first suture is threaded through said first primary and secondary channels.

6. The device of claim 5 wherein said cannula has a second primary channel extending axially therethrough and a second secondary channel extending from said second beveled surface to said second primary channel, and said second slide end of said second suture is threaded through said second primary and secondary channels.

7. The device of claim 6 wherein said first slip knot abuts the opening of said first secondary channel at said first beveled surface.

8. The device of claim 7 wherein said second slip knot abuts the opening of said second secondary channel at said second beveled surface.

9. The device of claim 8 wherein said first and second slide ends protrude from said proximal end of said cannula.

10. The device of claim 9 further comprising a first proximal knot on said first slide end, and a second proximal knot on said second slide end.

11. The device of claim 10 further comprising grasping means for pulling said first and second slide ends proximally, said grasping means slidably attached to said first and second slide ends between said proximal end of said cannula and said first proximal knot.

12. The device of claim 11 wherein said second slide end is longer than said first slide end by a length effective to prevent closing said second distal loop when said grasping means is pulled proximally against said first proximal knot so as to close said first distal loop.

13. The device of claim 12 wherein said grasping means is a molded pair of first and second beads, said first bead slidably attached to said first slide end, and said second bead slidably attached to said second slide end.

* * * * *